(12) United States Patent
Hausen et al.

(10) Patent No.: US 7,569,064 B1
(45) Date of Patent: Aug. 4, 2009

(54) APPARATUS AND METHOD FOR CLOSING AN ATRIAL APPENDAGE

(75) Inventors: Bernard A. Hausen, Menlo Park, CA (US); Bryan D. Knodel, Flagstaff, AZ (US); Brian R. DuBois, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 434 days.

(21) Appl. No.: 11/432,932

(22) Filed: May 12, 2006

Related U.S. Application Data

(60) Provisional application No. 60/680,862, filed on May 13, 2005.

(51) Int. Cl.
*A61B 17/08* (2006.01)
(52) U.S. Cl. ..................................... 606/151
(58) Field of Classification Search ............... 623/2.11; 606/151–158; 128/898
See application file for complete search history.

(56) References Cited

U.S. PATENT DOCUMENTS

| | | | |
|---|---|---|---|
| 5,306,234 A | | 4/1994 | Johnson |
| 5,549,621 A | * | 8/1996 | Bessler et al. ............... 606/151 |
| 5,865,791 A | | 2/1999 | Whayne et al. |
| 6,488,689 B1 | * | 12/2002 | Kaplan et al. ............... 606/139 |
| 6,966,919 B2 | * | 11/2005 | Sixto et al. .................. 606/153 |
| 6,991,643 B2 | | 1/2006 | Saadat |
| 2002/0062136 A1 | * | 5/2002 | Hillstead et al. ............ 606/205 |
| 2003/0045900 A1 | * | 3/2003 | Hahnen et al. .............. 606/205 |
| 2005/0033285 A1 | | 2/2005 | Swanson et al. |
| 2005/0149069 A1 | * | 7/2005 | Bertolero et al. ........... 606/151 |
| 2005/0277959 A1 | * | 12/2005 | Cosgrove et al. ........... 606/151 |

\* cited by examiner

*Primary Examiner*—(Jackie) Tan-Uyen T. Ho
*Assistant Examiner*—Melanie Tyson
(74) *Attorney, Agent, or Firm*—Brian A. Schar

(57) ABSTRACT

A surgical apparatus useful in closing an atrial appendage may include a clamp with a first arm and a second arm spaced apart from one another along at least a portion of their length, pins associated with the first arm, and a locking plate associated with the second arm. The clamp may have an open position in which the arms are spaced apart from one another, and a closed position in which the arms are closer to one another. To close the atrial appendage with the apparatus, the clamp in the open position may be placed relative to the atrial appendage such that it is located between the arms, and the clamp may be moved to the closed position, where that motion may cause the pins to penetrate the atrial appendage and engage the locking plate.

4 Claims, 4 Drawing Sheets

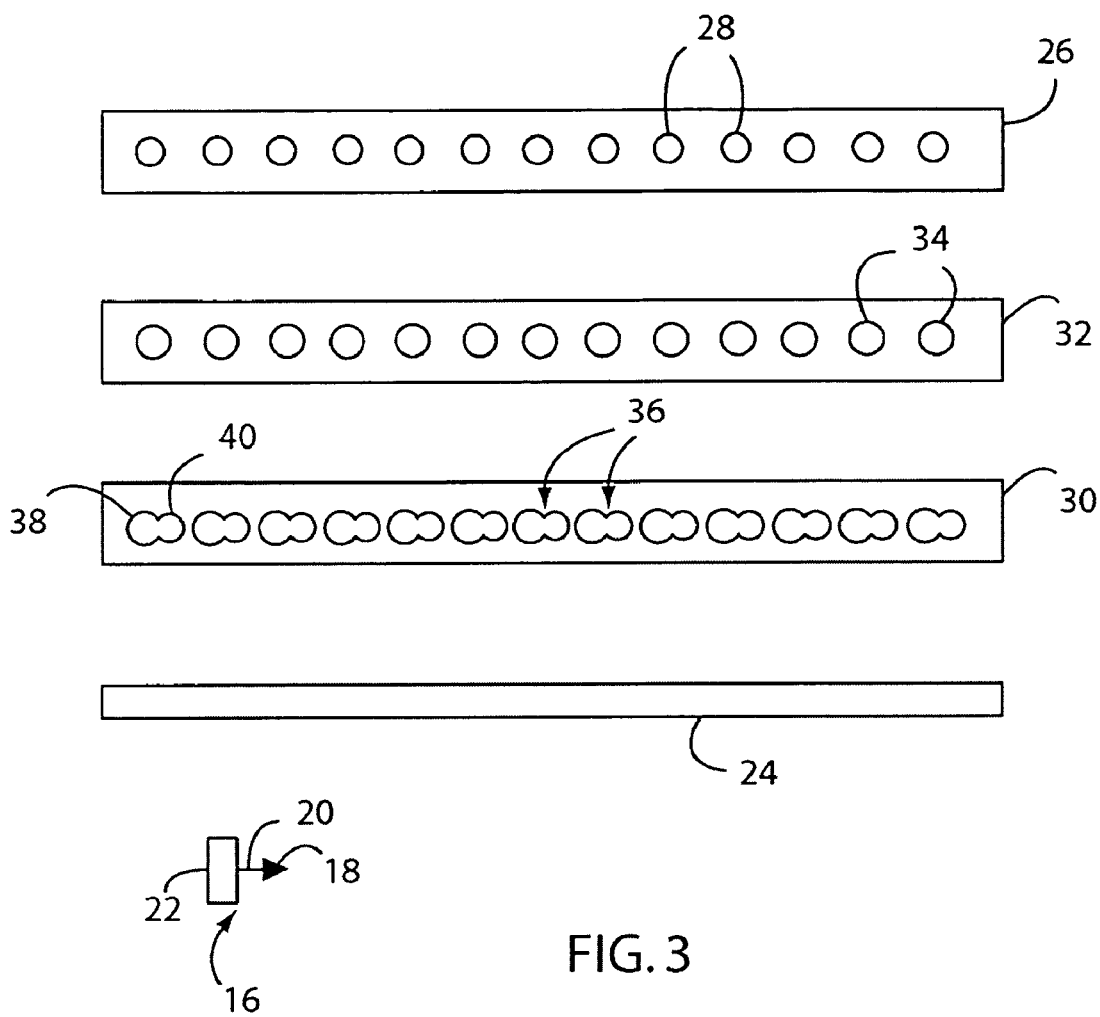
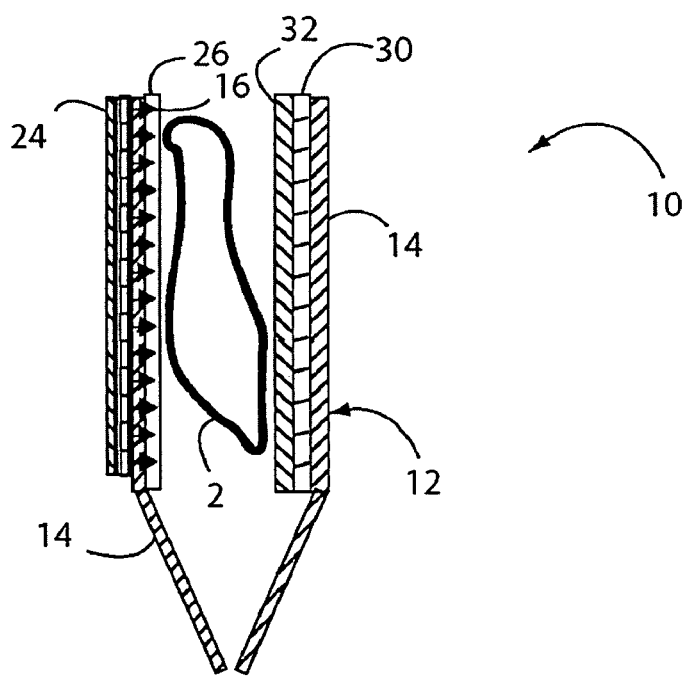

APPARATUS AND METHOD FOR CLOSING AN ATRIAL APPENDAGE

This application claims priority to U.S. Provisional Patent Application Ser. No. 60/680,862, filed on May 13, 2005, which is hereby incorporated by reference in its entirety.

FIELD OF THE INVENTION

The invention relates to an apparatus and method for performing cardiac surgery, and more specifically to an apparatus and method for closing an atrial appendage.

BACKGROUND

Referring to FIG. 1, the left atrial appendage (LAA) 2 is an anatomic feature of the human heart 4, and is a vestigial remainder of the embryo-stage left atrium. The LAA 2 is differently-sized in different patients, meaning that it may be trivial in some patients and relatively large in others. The LAA 2 is generally is positioned within the pericardial space of the heart. The LAA 2 is a sac-like feature that has an opening 6 connecting the interior space of the LAA 2 to the interior space of the left atrium 8. That opening 6 may be small compared with the interior of the LAA 2, which may cause blood to stagnate and then clot inside the LAA 2. Indeed, the LAA 2 is a major source of thrombi in patients with atrial fibrillation. These thrombi, when dislodged from the LAA 2, may cause stroke, which can debilitate or kill the patient.

BRIEF DESCRIPTION OF THE DRAWINGS

FIG. 2 is a top schematic view of a clamp assembly in an open position.

FIG. 3 is a top view of several components of the clamp assembly of FIG. 2.

The use of the same reference symbols in different figures indicates similar or identical items.

DETAILED DESCRIPTION

Figure 4:
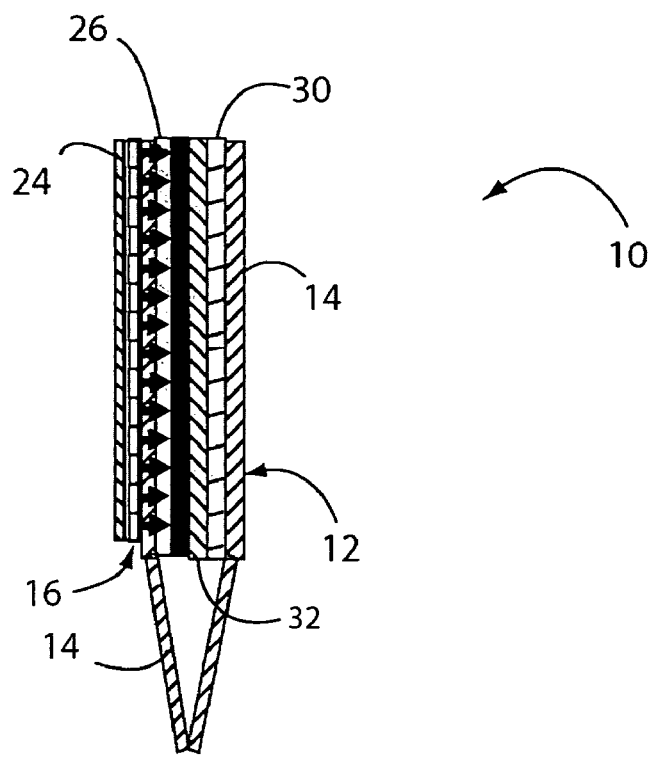
FIG. 4 is a top schematic view of the clamp assembly of FIG. 2 in a closed position.

Referring to FIG. 2, an exemplary clamp assembly 10 is shown. The clamp assembly 10 includes a clamp 12. The clamp 12 is movable from a first, open position, as shown in FIG. 2, to a second, closed position, as shown in FIG. 4, and back to the first position. Alternately, the clamp 12 is movable from the first to the second position, and not back to the first position. The clamp 12 includes at least two arms 14 spaced apart from one another along at least part of their length. The arms 14 are advantageously substantially linear and substantially parallel to one another, although the arms 14 may be shaped and/or aligned differently.

Referring also to FIG. 3, a plurality of pins 16 are associated with one arm 14 of the clamp 12. Each pin 16 may be configured in any suitable manner. As one example, at least one pin 16 may include a spike 18, which may be tapered and substantially radially symmetrical. Alternately, the spike 18 may be shaped and sized in any manner that allows it to penetrate tissue. A shaft 20 is connected to the rear of the spike 18. The width of the shaft 20 may be less than the width of the rear of the spike 18. A base 22 is connected to the end of the shaft 20 opposite the end of the shaft 20 connected to the spike 18. The base 22 is advantageously wider than the shaft 20, and may also be wider than the spike 18. The pins 16 may be all of substantially the same configuration, or at least some pins 16 may be of different configurations from one another. At least some of the pins 16 may be separate and independent from one another. Alternately, some or all of the pins 16 may be connected together in a pin assembly. Alternately, at least some of the pins 16 may be frangibly connected to one another, such that they are connected together before deployment and separated after deployment. The pins 16 may be fabricated from any suitable material, such as stainless steel or titanium alloy. Any suitable plastically-deformable, elastically-deformable or superelastically-deformable material may be used.

One arm 14 of the clamp 12 holds a plurality of the pins 16 in any suitable manner. As one example, the arm 14 may include one or more slots therein, where each slot allows at least one shaft 20 of a pin 16 to slide therethrough and therefore be released from the arm 14, as described in greater detail below. A wedge plate 24 is connected to the base 22 of each pin 16. Alternately, the wedge plate 24 is connected to the base 22 of less than all of the pins 16. The wedge plate 24 may be permanently connected to at least one pin 16, or may be detachable from at least one pin 16. Alternately, the wedge plate 24 may be omitted altogether. The wedge plate 24 acts to transmit force to the pins 16, to hold the pins 16 in place relative to the arm 14, and/or to hold the pins 16 together. Alternately, the wedge plate 24 may serve none of those functions, and/or may serve other functions. The wedge plate 24 may be thin and substantially rectangular. However, the wedge plate 24 may have any other suitable thickness and/or shape. The wedge plate 24 may be fabricated from any suitable biocompatible material, such as plastic, and advantageously are flexible. However, the wedge plate 24 may be rigid, if desired. The wedge plate 24, and the bases 22 of the pins 16, are advantageously positioned on an outer side of the corresponding arm 14. The "outer side" of the arm 14 is the side of a particular arm 14 that is not facing the other arm 14. The "inner side" of the arm 14 is the side of a particular arm 14 that is facing the other arm 14.

A load plate 26 is positioned on the inner side of the arm 14, on the opposite side from the wedge plate 24. The load plate 26 may be thin and substantially rectangular. However, the load plate 26 may have any other suitable thickness and/or shape. The load plate 26 may be fabricated from any suitable biocompatible material, such as plastic, and advantageously is flexible. However, the load plate 26 may be rigid, if desired. The load plate 26 includes a plurality of apertures 28 defined therethrough. Each aperture 28 is substantially the same size and shape as the cross-section of the shaft 20 of the corresponding pin 16. Thus, if the shaft 20 is circular in cross-section and substantially 1 mm in diameter, then the corresponding aperture 28 in the load plate 26 is substantially circular and slightly larger than 1 mm in diameter. However, the apertures 28 may be sized and shaped in a different manner, if desired. The load plate 26 acts as a gasket, as described in greater detail below. Alternately, the load plate 26 may serve a different, or one or more additional, functions, or may be omitted altogether.

A locking plate 30 is detachably connected to the inner side of the other arm 14 in any suitable manner. Advantageously, the locking plate 30 is slidable in the longitudinal direction relative to the corresponding arm 14. In turn, a counter plate 32 is connected to the inner side of the locking plate 30. The locking plate 30 is advantageously slidable in the longitudinal direction relative to the counter plate 32 as well. Thus, the counter plate 32 may be attached directly to the corresponding arm 14. The locking plate 30 and the counter plate 32 are both detachable from the corresponding arm 14. The counter plate 32 may be thin and substantially rectangular. However, the counter plate 32 may have any other suitable thickness and/or shape. The counter plate 32 may be fabricated from any suitable biocompatible material, such as plastic, and advantageously is flexible. However, the counter plate 32 may be rigid, if desired. The counter plate 32 includes a plurality of apertures 34 defined therethrough. The apertures 34 of the counter plate 32 are larger than the corresponding apertures 28 of the load plate 26, and are substantially aligned with the apertures 28 of the load plate 26. Each aperture 34 is sized to receive a corresponding spike 18 of a pin 16, and may be sized as wide as the widest point of the corresponding spike 18 and shaped in the same manner as the cross section of the corresponding spike 18. Alternately, the apertures 34 of the counter plate 32 are the same size as the apertures 28 of the load plate 26. Alternately, the counter plate 32 does not have apertures therethrough. The counter plate 32 acts as a gasket, as described in greater detail below. Alternately, the counter plate 32 may serve a different, or one or more additional, functions, or may be omitted altogether.

The locking plate 30 may be thin and substantially rectangular. However, the locking plate 30 may have any other suitable thickness and/or shape. The locking plate 30 may be fabricated from any suitable biocompatible material, such as plastic, and advantageously is substantially rigid. However, the locking plate 30 may be flexible, if desired. The locking plate 30 includes a plurality of keyhole apertures 36 defined therethrough. Each keyhole aperture 36 may have a complex shape with two major components. The first component 38 is an opening substantially the same width and cross-sectional shape as the widest point of the corresponding spike 18. In this way, the first component 38 of the keyhole aperture 36 can receive the spike 18 of the corresponding pin 16, as described in greater detail below. The second component 40 of the keyhole aperture 36 is an opening substantially the same width and cross-sectional shape as the shaft 20 of the corresponding pin 16, as described in greater detail below. The second component 40 of the keyhole aperture 36 is smaller than the first component 38. Advantageously, the interface between the first component 38 and the second component 40 is slightly narrower than the width of the shaft 20 of the corresponding pin 16.

Operation

Figure 1:
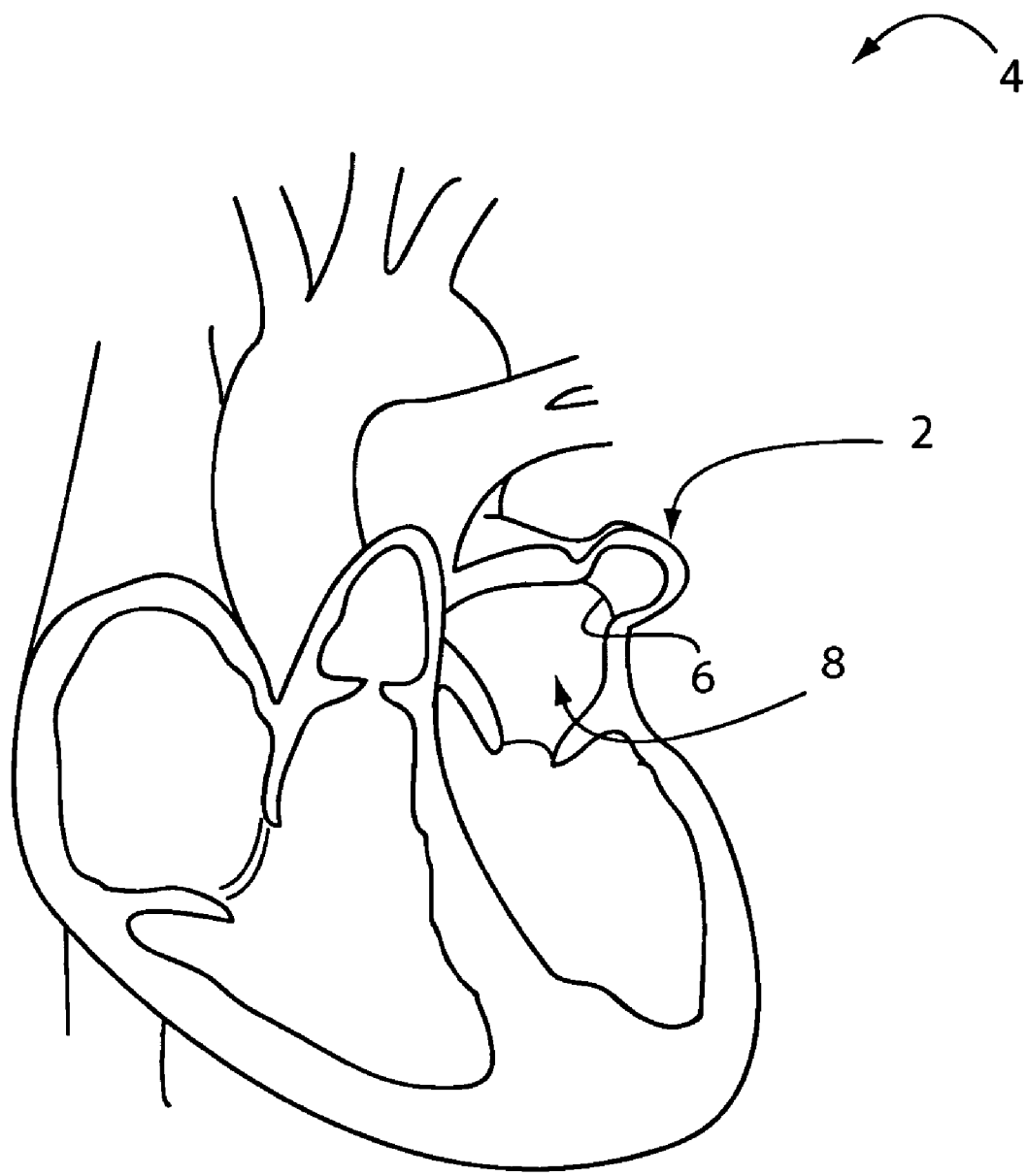
FIG. 1 is a cross-section view of a human heart that has an LAA.

Operation of the clamp assembly 10 is described in terms of closing a left atrial appendage. This description is provided for convenience and brevity only, and does not limit the use of the clamp assembly 10. Referring to FIG. 2, the clamp assembly 10 is inserted into the patient in the open position. The clamp assembly 10 may be connected to an actuator (not shown), at least part of which may extend out of the patient. The actuator may be any mechanism that is capable of manipulating the clamp assembly 10 in the manner described below, and may utilize stored energy, such as energy in the form of compressed gas or a compressed spring. Alternately, the actuator may be omitted, and the clamp assembly 10 may be directly actuated by hand by the surgeon. The clamp assembly 10 is placed relative to the LAA 2 such that the LAA 2 is positioned between the arms 14 of the clamp 12. Advantageously, referring also to FIG. 1, the clamp assembly 10 is placed close to, or at least partially on, the exterior surface of the left atrium 8.

Referring also to FIG. 4, the clamp 12 is closed onto the LAA 2 in any suitable manner. As the clamp 12 is closed onto the LAA 2, the arms 14 move toward one another, and the spikes 18 of the pins 16 are brought into contact with the LAA 2. The spikes 18 may penetrate into the LAA 2 as they are moved toward it. The arms 14 move closer together until the LAA 2 is compressed between them and the arms 14 cannot move substantially closer to each other. The LAA 2 may be substantially flattened after the clamp 12 is closed upon it, or may simply be compressed relative to its original shape. Alternately, the arms 14 are moved to a position in which they are a preselected distance apart from one another.

Figure 5:
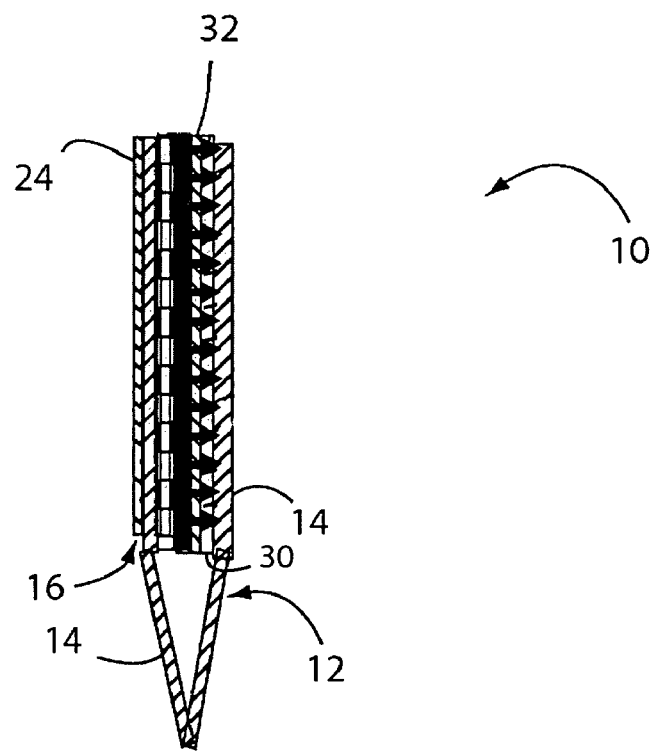
FIG. 5 is a top schematic view of the clamp assembly of FIG. 2, illustrating penetration of an anatomic feature by pins included in the clamp assembly.

Referring also to FIGS. 3 and 5, after the clamp 12 has been closed, the wedge plate 24 is urged toward the opposite arm 14. As a result, the wedge plate 24 exerts a force on the bases of the pins 16, and urges the pins 16 toward the opposite arm 14. As the pins 16 move toward the opposite arm 14, the spikes 18 move toward the opposite arm 14. The force exerted on the pins 16 pushes the spikes 18 out of the corresponding apertures in the load plate 26, and then pushes the spikes 18 through the compressed tissue of the LAA 2. The spikes 18 continue to move through the LAA 2, and emerge from the other side. Each spike 18 continues to move into a corresponding aperture 34 in the counter plate 32, and then into a corresponding first component 38 of a keyhole aperture 36 in the locking plate 30. The first component 38 of each keyhole aperture 36 of the locking plate 30 is advantageously substantially aligned with an aperture 34 in the counter plate 32 to facilitate this motion of the spike 18. The pins 16 continue to move until each shaft 20 is located within a corresponding first component 38 of a keyhole aperture 36. Alternately, the pins 16 stop moving when each spike 18 is located within a corresponding first component 38 of a keyhole aperture 36, and the shafts 20 of the pins 16 remain outside the keyhole apertures 36. Alternately, where the counter plate 32 does not include apertures defined therein, the spikes 18 puncture the counter plate 32, and each spike 18 continues its motion into the corresponding first component 38 of the keyhole aperture 36 of the locking plate 30. Alternately, where the wedge plate 24 is omitted, the bases 22 of the pins 16 are urged directly toward the opposite arm 14, and the motion of the spikes 18 is substantially as described above.

Figure 6:
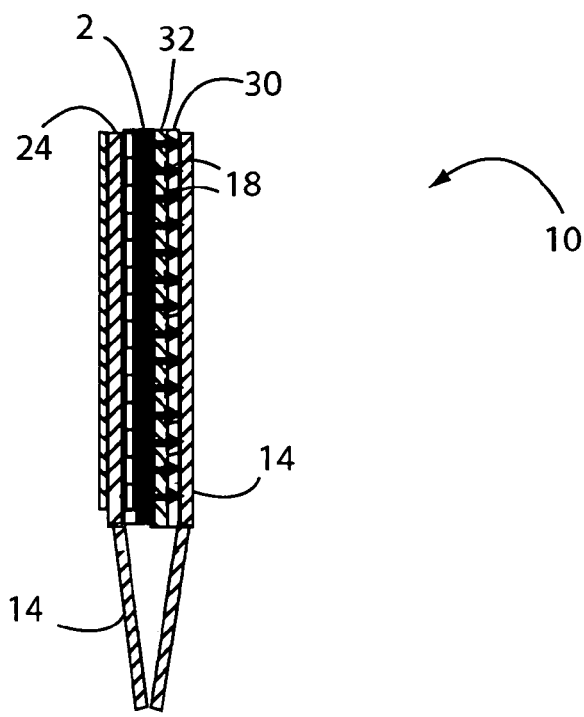
FIG. 6 is a top schematic view of the clamp assembly of FIG. 2, illustrating locking of the pins by a locking plate included in the clamp assembly.

Referring also to FIG. 6, the locking plate 30 is then slid longitudinally relative to the arm 14. Alternately, the locking plate 30 is moved in a different manner in order to lock the pins 16 in place. As a result, the second component 40 of each keyhole aperture 36 in the locking plate 30 is slid toward the corresponding shaft 20 of the corresponding pin 16. Advantageously, the interface between the first component 38 and the second component 40 is slightly narrower than the width of the shaft 20 of the corresponding pin 16, as described above. Thus, as the locking plate 30 moves, each second component 40 of a keyhole aperture 36 is forced toward the corresponding shaft 20. This force causes the locking plate 30 in the vicinity of the interface between the first component 38 and the second component 40, or the shaft 20, or both, to flex. As a result, the shaft 20 snaps into the second component 40 of the keyhole aperture 36, locking the shaft 20 and thus the pin 16 into place relative to the locking plate. The width of the spike 18 compared to the narrower width of the second component 40 of the keyhole aperture prevents each pin 16 from pulling out of the locking plate 30.

Figure 7:
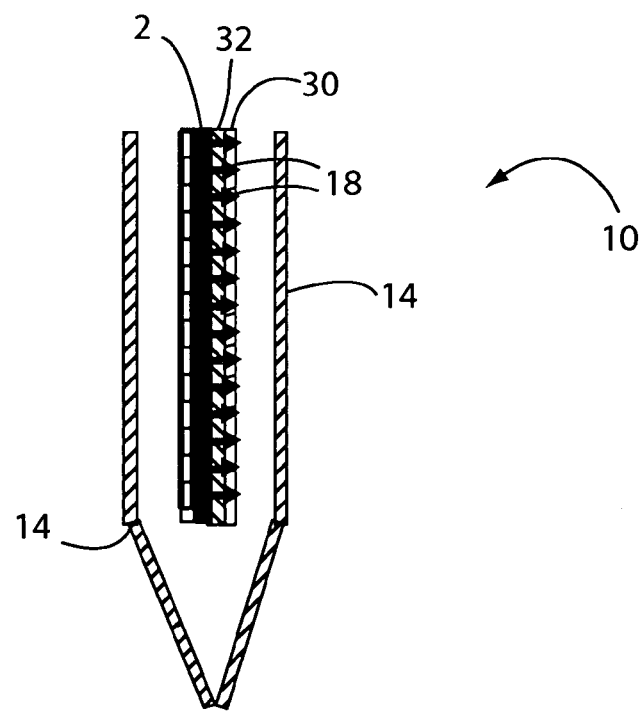
FIG. 7 is a top schematic view of the clamp of the clamp assembly of FIG. 2 in a closed position, after releasing particular components of the clamp assembly.

Referring to FIGS. 3 and 7, with the pins 16 locked in place relative to the locking plate, the LAA 2 has been closed. The counter plate 32 and locking plate 30 may act as gaskets. The clamp 12 is then moved back to the open position, releasing the pins 16 and plates 24, 26, 30, 32. Each arm 14 of the clamp 12 may include one or more slots therein, where the slot or slots allow the pins 16 to be released from that arm 14. As one example, each arm 14 may simply include one linear slot along its length, and each arm 14 may be slid off the pins 16 prior to opening the clamp 12. Alternately, the pins 16 and the locking plate 30 may be detached from the clamp 12 in any other suitable manner. Alternately, the clamp 14 remains in the closed position, and remains in the patient. If so, a ratchet or other feature may be provided, such that the clamp can continue to exert a clamping force on the LAA 2.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Further, the invention is not limited to closing the LAA. The invention may be utilized, for example, to close the right atrial appendage, other defects of the heart, or appendages in other areas of the body. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical method, comprising:
    providing a clamp assembly, comprising a clamp including a first arm and a second arm, wherein said arms are spaced apart along at least a portion of their length; a plurality of pins associated with said first arm; and a locking plate associated with said second arm; wherein said clamp is movable from an open position to a closed position;
    placing said clamp in said open position relative to an anatomic feature such that the anatomic feature is located between said arms; and
    moving said clamp to said closed position, wherein said moving causes said pins to penetrate through the anatomic feature and into said locking plate; and
    moving said locking plate relative to said pins after said moving said clamp to said closed position; wherein said moving said locking plate locks said pins in place relative to said locking plate;
    wherein said clamp is held in said closed position as a consequence of said moving said locking plate.

2. The method of claim 1, wherein said anatomic feature is a left atrial appendage connected to the left atrium of the heart.

3. The method of claim 2, wherein said placing further comprises placing said clamp in said open position on the left atrium.

4. The method of claim 1, wherein said moving said locking plate comprises sliding said locking plate.

* * * * *